United States Patent
Tian et al.

(10) Patent No.: US 7,740,747 B2
(45) Date of Patent: Jun. 22, 2010

(54) INJECTION METHOD FOR MICROFLUIDIC CHIPS

(75) Inventors: Wei-Cheng Tian, Clifton Park, NY (US); Erin Jean Finehout, Clifton Park, NY (US); Li Zhu, Clifton Park, NY (US); Jun Xie, Niskayuna, NY (US); Shashi Thutupalli, Bangalore (IN)

(73) Assignee: General Electric Company, Niskayuna, NY (US)

( * ) Notice: Subject to any disclaimer, the term of this patent is extended or adjusted under 35 U.S.C. 154(b) by 153 days.

(21) Appl. No.: 11/965,794

(22) Filed: Dec. 28, 2007

(65) Prior Publication Data

US 2009/0166203 A1 Jul. 2, 2009

(51) Int. Cl.
*G01N 27/26* (2006.01)

(52) U.S. Cl. .............. 204/453; 204/450; 204/451; 204/454; 204/455; 204/456; 204/600; 204/601; 204/604; 435/283.1; 435/286.5; 435/287.3; 435/288.2

(58) Field of Classification Search ......... 204/450–456, 204/604, 400, 193, 194, 601; 205/775; 251/30.01; 435/283.1, 286.5, 287.3, 288.2
See application file for complete search history.

(56) References Cited

U.S. PATENT DOCUMENTS

| | | | |
|---|---|---|---|
| 4,879,247 A | 11/1989 | Ohlson | |
| 4,908,112 A | 3/1990 | Pace | |
| 5,077,017 A * | 12/1991 | Gorin et al. | 422/100 |
| 5,644,395 A | 7/1997 | Folta | |
| 5,824,204 A | 10/1998 | Jerman | |
| 5,976,336 A | 11/1999 | Dubrow et al. | |
| 6,001,229 A | 12/1999 | Ramsey | |
| 6,010,607 A | 1/2000 | Ramsey | |

(Continued)

FOREIGN PATENT DOCUMENTS

EP 0268406 A2 11/1987

(Continued)

OTHER PUBLICATIONS

P.F. Man, D.K. Jones and C.H. Mastrangelo; "Microfluidic Plastic Capillaries on Silicon Substrates: A New Inexpensive Technology for Bioanalysis Chips"; Center for Integrated Sensors and Circuits, Department of Electrical Engineering and Computer Science, University of Michigan, Ann Arbor, MI 48109-2122, USA; 0-7803-3744-1/97/$5.00 0 1997 IEEE; On pp. 311-316.

(Continued)

*Primary Examiner*—Nam X Nguyen
*Assistant Examiner*—Jennifer Dieterle
(74) *Attorney, Agent, or Firm*—Jenifer E. Haeckl

(57) ABSTRACT

A microchip for capillary electrophoresis is provided. The microchip comprises an injection channel and a separation channel configured to receive a sample through a sample well disposed on a first end of the separation channel; wherein the injection channel and the separation channel intersect to form a 'T' junction. The microchip further comprises a first valve disposed adjacent to the 'T' junction and on the separation channel and a second valve disposed at the 'T' junction. The second valve is a two-way valve. A sample plug is injected into an area between the 'T' junction and a second end of the separation channel.

12 Claims, 2 Drawing Sheets

U.S. PATENT DOCUMENTS

Figure 1:
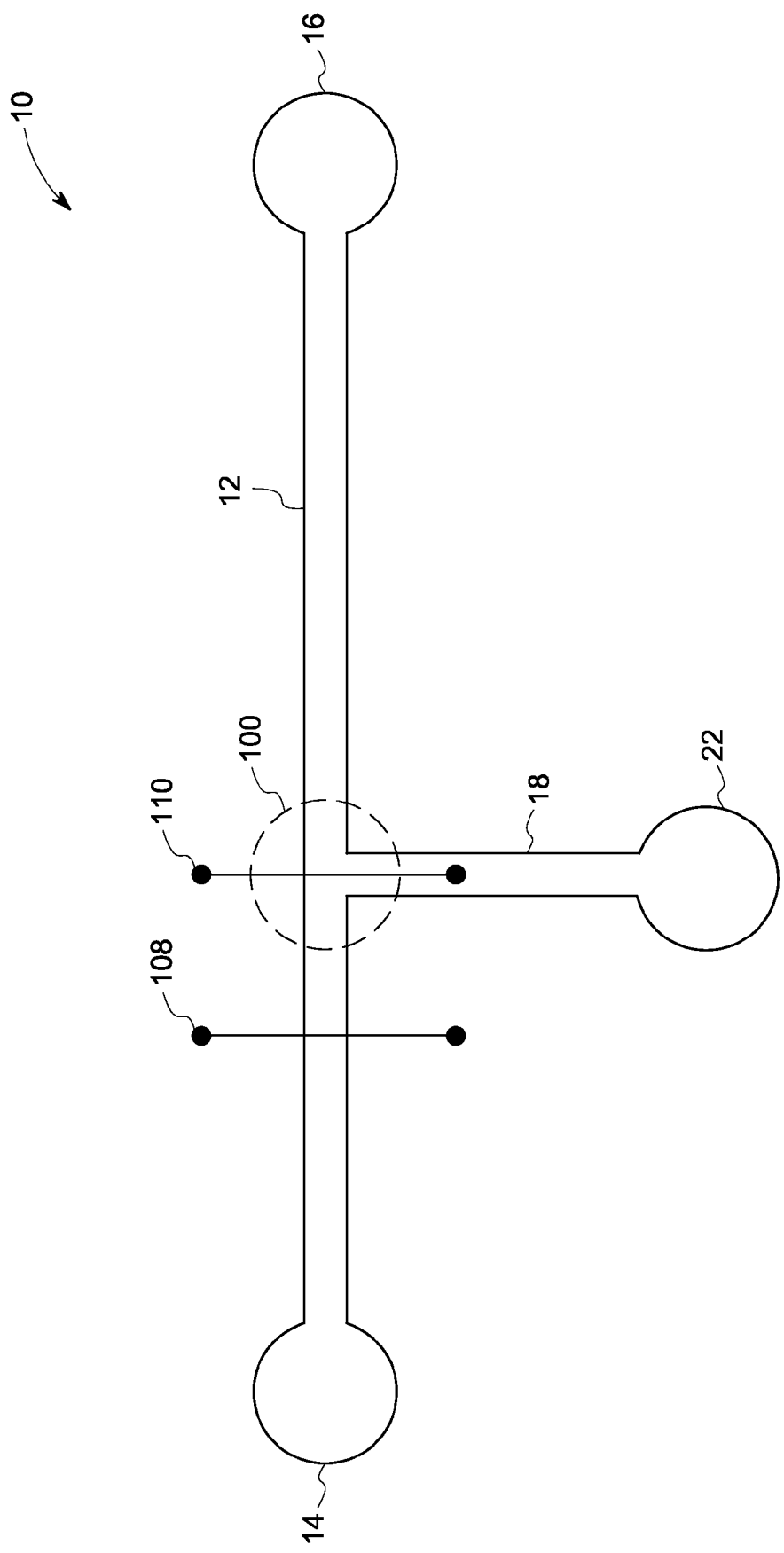

| | | | |
|---|---|---|---|
| 6,056,859 A | 5/2000 | Ramsey et al. | |
| 6,210,986 B1 | 4/2001 | Arnold et al. | |
| 6,251,343 B1 | 6/2001 | Dubrow et al. | |
| 6,280,589 B1 | 8/2001 | Manz | |
| 6,432,290 B1 | 8/2002 | Harrison et al. | |
| 7,005,050 B2 * | 2/2006 | Burns et al. | 204/453 |
| 7,214,298 B2 * | 5/2007 | Spence et al. | 204/450 |
| 2001/0035351 A1 * | 11/2001 | Simpson et al. | 204/453 |
| 2002/0197736 A1 | 12/2002 | Amirkhanian | |
| 2003/0215855 A1 | 11/2003 | Dubrow et al. | |
| 2003/0230486 A1 | 12/2003 | Chien et al. | |
| 2004/0195099 A1 | 10/2004 | Jacobson et al. | |
| 2005/0006238 A1 | 1/2005 | Jaffe | |
| 2006/0042948 A1 | 3/2006 | Santiago et al. | |
| 2006/0147344 A1 | 7/2006 | Ahn | |
| 2006/0169588 A1 | 8/2006 | Jacobson et al. | |

FOREIGN PATENT DOCUMENTS

| | | |
|---|---|---|
| WO | 96/04547 A1 | 2/1996 |
| WO | 99/34220 A2 | 7/1999 |
| WO | 9966318 A1 | 12/1999 |
| WO | 0131322 A1 | 5/2001 |
| WO | 0170397 A2 | 9/2001 |
| WO | 03084629 A2 | 10/2003 |
| WO | 2005118138 A1 | 12/2005 |

OTHER PUBLICATIONS

Pei Yu Chiou, Aaron T.Ohta and Ming C. Wu; "Massively parallel manipulation of single cells and microparticles using optical images"; Nature 436, 370-372 (Jul. 21, 2005) | doi: 10.1038/nature03831.

D. Huh et al., "Microfluidics for Flow Cytometric Analysis of Cells and Particles", Physiol. Meas. 26, R73-R98 (2005).

R. Johann et al., "A Simple Mechanism for Reliable Particle Sorting in a Microdevice With Combined Electroosmostic and Pressure-Driven Flow", Electrophoresis, vol. 25, pp. 3720-3729 (2004).

F. Lacharme et al., "Pressure Injection in Continuous Sample Flow Electrophoresis Microchips", Sensors & Actuators B: Chemical, vol. 117, Issue 2, pp. 384-390 (Oct. 2006).

Y. Lin et al., "A Poly-methylmethacrylate Electrophoresis Microchip with Sample Preconcentrator", J. Micromech. & Microeng., vol. 11, pp. 189-194 (2001).

R. Ma et al., "A Rapid performance Assessment Method for Microfluidic Chips", Proceedings of the 2004 International Conf. on MEMS, NANO and Smart Systems, IEEE, pp. 1-7 (2004).

R. Schlund et al., "Continuous Sampling and Analysis by On-Chip Liquid/Solid Chromatography", Sensors & Actuators: B Chemical, vol. 123, No. 2, pp. 1133-1141 (2007).

* cited by examiner

INJECTION METHOD FOR MICROFLUIDIC CHIPS

BACKGROUND

The invention relates generally to microfluidic chips and more specifically to injection methods for microfluidic chips.

Electrophoretic separation of bio-molecules is very important in modern biology and biotechnology applications such as DNA sequencing, protein analysis and genetic mapping. Electrophoresis is a process by which individual molecular species are separated in a conductive medium (such as a liquid solution or a cross-linked polymer) by applying an electric field. The charged molecules migrate through the media and separate into distinct bands due to their mobility difference. The rates are influenced by factors such as a viscosity of the media, a mass and charge of the molecules, and a strength and duration of the electric field.

An increase in a voltage gradient (V/cm) applied to the electrophoretic device results in a corresponding decrease in the time needed to perform the separation. However, increasing the voltage gradient is governed by certain constraints. For example, increasing the voltage gradient beyond a certain point may result in an increase in joule heating which would in turn alter the properties of the medium in which the molecules are being separated. The change of the medium properties leads to an increase in sample diffusion and thus degraded the separation resolution. In order to alleviate the above limitations, electrophoresis can be performed in a capillary or miniaturized channel. The large surface-area-to-volume ratio of the electrophoretic devices offers efficient dissipation of Joule heat, allowing higher electric field to be used, thus resulting in the shorter analysis time and better separation efficiency.

Microchips are small microfluidic devices that perform chemical and physical operations such as capillary electrophoresis with microscale sample volumes. These devices often have the benefits of fast reactions, rapid detection, small reagent consumption, ease of automation and simple transfer between reaction vessels. Microfluidic devices are commonly referred to as "lab-on-a-chip."

In microchip electrophoresis, a sample is loaded in a sample reservoir and a voltage is applied between a sample reservoir and a waste reservoir to move sample into the loading channel. However, proteins with different mobilities may result in a biased injection, in which the sample injected into the separation channel does not represent the original sample composition. A long time injection is usually applied to overcome this problem.

Therefore, there is a need for a microfluidic device that provides a fast sample loading technique where the sample composition is uniform at the injection point.

BRIEF DESCRIPTION

Briefly, according to one embodiment of the invention a microchip for electrophoresis is provided. The microchip comprises a separation channel comprising a first end and a second end. The microchip further comprises an injection channel comprising a first end and configured to receive a sample through a sample well disposed on the first end of the separation channel. The injection channel and the separation channel intersect to form a 'T' junction. The microchip further comprises a first valve disposed adjacent to the 'T' junction and on the separation channel between the 'T' junction and the first end of the separation channel and a second valve disposed at the 'T' junction; wherein a sample plug is injected into an area between the 'T' junction and the second end of the separation channel. The sample plug is defined by an area between the first valve and the second valve.

In another embodiment, a method for electrophoresis is provided. The method comprises forming an injection channel, forming a separation channel; wherein the injection channel and the separation channel intersect to form a 'T' junction. The method further comprises disposing a first valve between a first end of the separation channel and the 'T' junction on the separation channel, disposing a second valve at the 'T' junction and separating a portion of the sample into an area between the 'T' junction and a second end of the separation channel during electrophoresis.

DRAWINGS

Figure 2:
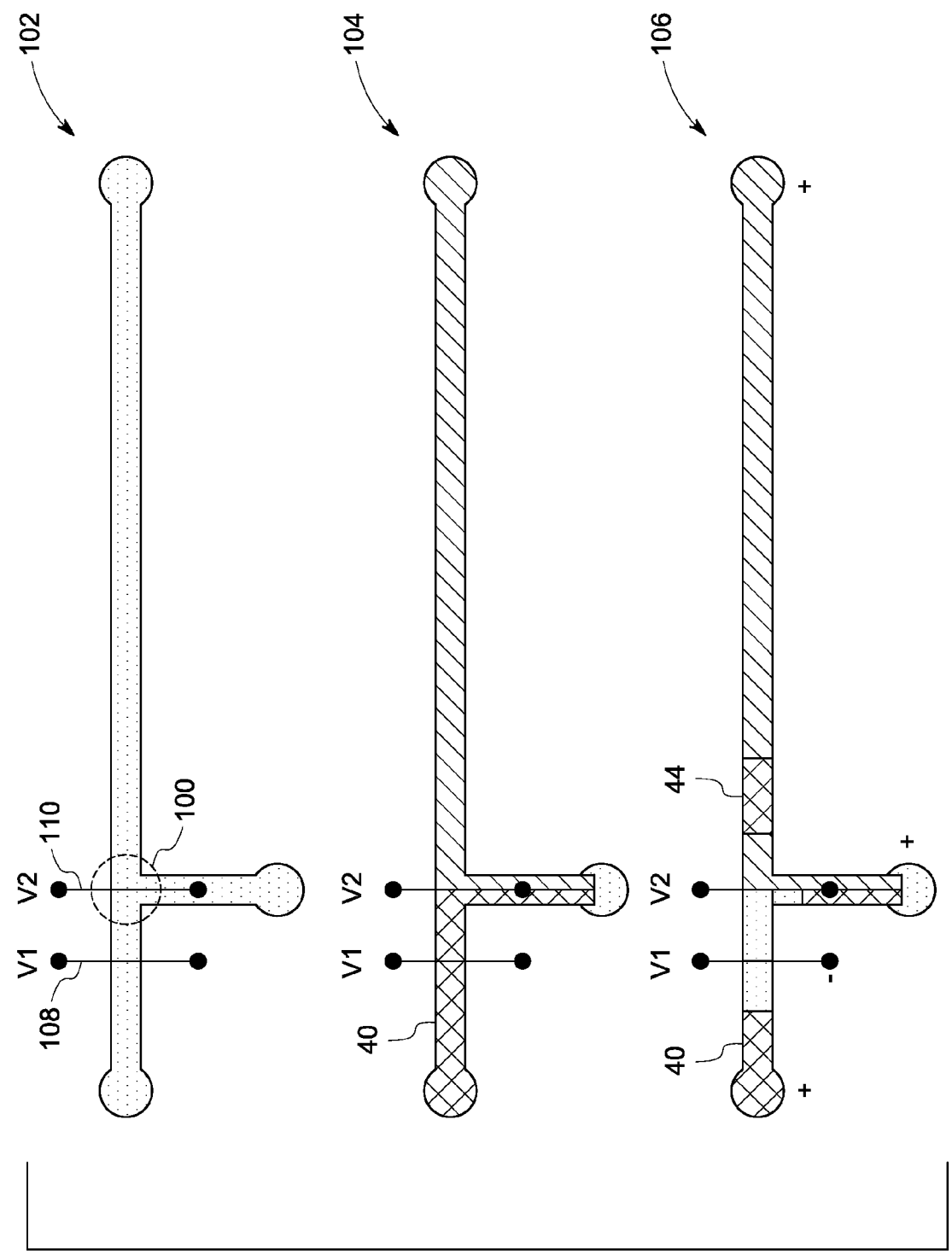

These and other features, aspects, and advantages of the present invention will become better understood when the following detailed description is read with reference to the accompanying drawings in which like characters represent like parts throughout the drawings, wherein:

FIG. 1 is a block diagram of one embodiment of a microchip implemented according to one aspect of the invention; and FIG. 2 is a flow chart illustrating one method by which a sample can be injected into a microchip device.

DETAILED DESCRIPTION

FIG. 1 is a block diagram of one embodiment of a microchip implemented according to one aspect of the invention. Each component of the microchip device is described in further detail below.

Microchip 10 comprises an injection channel 18 and separation channel 12. Separation channel 12 comprises a first end and a second end. Wells 14 and 16 are disposed over the first end and the second end respectively. The injection channel and the separation channel intersect to form a 'T' junction 100. The injection channel 18 comprises first end and is configured to receive a sample through a sample well 22 disposed over the first end of the separation channel.

First valve 108 is disposed adjacent to the 'T' junction 108 and between the 'T' junction and the first end of the separation channel 12. Second valve 110 disposed at the 'T' junction 108. The second valve is a two-way valve. As used herein, a two-way valve refers to a valve that is operable to close in a horizontal direction and a vertical direction. During electrophoresis, a sample plug is injected into an area between the 'T' junction and well 16. In one embodiment, the sample plug is defined by an area between the first valve and the second valve. In a specific embodiment, both first valve and second valve function as electrodes.

When the second valve is closed in a vertical direction, no direct fluid communication exists between the first end and the second end of the separation channel. When the second valve is closed in horizontal direction, no direct fluid communication exists between the first end/second end of the separation channel and the injection channel. However, the first end of the injection channel and the first end of the separation channel remain in fluid connection. Similarly, the first end of the injection channel and the second end of the separation channel also remain in fluid connection The manner in which the sample is analyzed is described in further detail below.

FIG. 2 is a flow chart illustrating one method by which a sample can be injected into a microchip device. The following technique is adapted for use in microchips having the injection channel and the sample channel forming a three-way junction or a 'T' junction. Each step is described in further detail below.

In step 102, a first valve is disposed adjacent to the 'T' junction and between the 'T' junction and the first end of the separation channel and a second valve is disposed at the 'T' junction. The valves are operable to be opened and closed at different instances of time. During electrophoresis, a portion of the sample plug is injected into an area between the 'T' junction and the end of the separation channel.

In step 104, the sample 40 is loaded into the injection channel by opening the first valve and the second valve. Similarly, a sieving matrix is loaded into the separation channel through well 16. The sieving matrix occupies the area after the 'T' junction. In one embodiment, a predetermined amount of the sieving matrix is loaded into the separation channel. In another embodiment, the separation channel is partially loaded with a predetermined amount of the sieving matrix.

In step 106, a portion of the sample 44 is injected into the separation channel by applying a separation voltage across the first valve 108 and the second end of the separation channel while simultaneously closing the second valve 110 in the vertical direction and closing the first valve 108. In a further embodiment, a pull back voltage is applied between the well 14 and well 22 of the injection channel.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A microchip for capillary electrophoresis, the microchip comprising:
   a separation channel comprising a first end and a second end, said second end being adapted to deliver an electrical potential;
   an injection channel comprising a first end and configured to receive a sample through a sample well disposed on the first end of the separation channel, said first end being adapted to deliver an electrical potential; wherein the injection channel and the separation channel intersect to form a 'T' junction; wherein a sieving matrix occupies a region after the 'T' junction;
   a first valve disposed adjacent to the 'T' junction and on the separation channel between the 'T' junction and the first end of the separation channel and adapted to deliver an electrical potential; and
   a second valve disposed at the 'T' junction; wherein the second valve is a two-way valve; said valve being adapted to be positioned to either preclude flow between said first end of said separation channel and said second end of said separation channel or to preclude flow between said injection channel and said separation channel and to deliver an electric potential.

2. The microchip of claim 1, wherein the first valve is open and the second valve is closed to flow between said first end of said separation channel and said second end of said separation channel.

3. The microchip of claim 2, wherein a sieving matrix is loaded to the separation channel.

4. The microchip of claim 1, wherein a voltage is maintained across the first valve and the second end of the separation channel and the second valve is closed to flow between said injection channel and said separation channel and the first valve is closed.

5. The microchip of claim 1, wherein loading the sieving matrix comprises loading a predetermined amount of the sieving matrix.

6. The microchip of claim 1, wherein the separation channel is partially loaded with a predetermined amount of the sieving matrix.

7. The microchip claim 1, wherein a portion of the sample that injects into the separation channel is defined by an area between the first valve and the second valve.

8. A method for electrophoresis, the method comprising:
   forming an injection channel comprising a first end and configured to receive a sample through a sample well disposed on the first end of the separation channel;
   forming a separation channel comprising a first end and a second end; wherein the injection channel and the separation channel intersect to form a 'T' junction;
   disposing a first valve between a first end of the separation channel and the 'T' junction on the separation channel;
   disposing a second valve at the 'T' junction; wherein the second valve is a two-way valve; said valve being adapted to be positioned to either preclude flow between said first end of said separation channel and said second end of said separation channel or to preclude flow between said injection channel and said separation channel;
   loading a sample into said first end of said injection channel;
   opening said first valve and operating said second valve to preclude flow between said first end of said separation channel and said second end of said separation channel and using electrical potential to draw said sample into said first end of said separation channel;
   closing said first valve and operating said second valve to allow flow between said first end of said separation channel and said second end of said separation channel and to preclude flow between said injection channel and said separation channel; and
   injecting a portion of the sample into an area between the 'T' junction and a second end of the separation channel using an electrical potential between said first valve and said second end of said separation channel.

9. The method of claim 8, further comprising loading a sample into the separation channel by opening the first valve and closing the second valve in a vertical direction.

10. The method of claim 8, further comprising applying a voltage across said first valve and said second end of said separation channel while simultaneously opening said second valve to allow flow between said first end of said separation channel and said second end of said separation channel and closing said first valve.

11. The method of claim 8, wherein the step of separating comprises applying a voltage across the first valve and the second end of the separation channel while simultaneously opening the second valve to allow flow between said first end of said separation channel and said second end of said separation channel and closing the first valve.

12. The method of claim 11, further comprising applying a pull back voltage between the first end of the separation channel and the injection channel.

* * * * *